United States Patent
Michalski et al.

(12) 
(10) Patent No.: US 6,479,656 B1
(45) Date of Patent: Nov. 12, 2002

(54) PHOSPHORYLATION PROCESS AND CATALYST

(75) Inventors: Jan Michalski; Wojciech Dabkowski; Friedrich Cramer, all of Sienkiewicza (PL)

(73) Assignees: Perstorp AB, Perstorp (SE); Polish Academy of Science, Centre of Molecular and Macromolecular Studies, Lolz (PL)

( * ) Notice: Subject to any disclaimer, the term of this patent is extended or adjusted under 35 U.S.C. 154(b) by 0 days.

(21) Appl. No.: 09/688,184

(22) Filed: Oct. 16, 2000

Related U.S. Application Data

(63) Continuation of application No. 09/142,846, filed as application No. PCT/SE97/00345 on Feb. 28, 1997, now abandoned.

(30) Foreign Application Priority Data

Mar. 18, 1996 (SE) ................................................ 9601016

(51) Int. Cl.$^7$ ................................................ C07H 21/00
(52) U.S. Cl. ................................ 536/25.34; 536/25.33
(58) Field of Search ........................... 536/25.33, 25.34; 558/70

(56) References Cited

U.S. PATENT DOCUMENTS 5,159,095 A * 10/1992 Celebuski .................... 556/436

FOREIGN PATENT DOCUMENTS

| WO | 9221689 | * | 12/1992 |
| WO | WO97/34853 A1 | * | 9/1997 |

OTHER PUBLICATIONS

Cramer, "Recent Methods of Phosphorylation and Their Application to Nucleotide Chemistry," presented at *Chimie Organique du Phosphore, 182nd Colloques Internationaux du Centre National de la Recherche Scientifique*, Paris, France, May 19–24, 1969; published in English by Éditions du Centre National de la Recherche Scientific, 1970, pp. 344–352.*

Dabkowski et al., "Silyloxyphosphanes. New Phosphitylating Reagents in Nucleotide Chemistry," *Nucleosides & Nucleotides*, 10(1–3), 601–602 (1991).*

Prisbe et al., "The Phosphorylation of an Acyclic Nucleoside Using Stannic Chloride as a Solubilizing Agent," Section IV of *Nucleic Acid Chemistry—New and Improved Procedures, Methods and Techniques, Part Four*, Townsend and Tipson (eds.), John Wiley & Sons, New York, NY, 1991, pp. 341–343.*

Duthaler et al., "159. Preparation of Regioselectively Protected Hydroquinones by Phosphorylation of p–Benzoquinones with Trialkyl Phosphites," *Helvetica Chimica Acta*, 67, 1406–1426 (1984).*

* cited by examiner

*Primary Examiner*—James O. Wilson
*Assistant Examiner*—L. E. Crane
(74) *Attorney, Agent, or Firm*—Stevens, Davis, Miller & Mosher, L.L.P.

(57) ABSTRACT

A process and use of at least one catalyst for phosphorylation, in particular phosphitylation, of hydroxyl groups, whereby a phosphorous compound is added to a hydroxyfunctional compound having at least one hydroxyl group. The addition yields a phosphorylated product having at least one O—P bond. The catalyst employed in the process is of the general formula $(R^1)_n X(R^2)_{4-n}$, wherein each $R^1$ independently is hydrogen, at least one hydrocarbyl, amino, halogenated and/or silylated hydrocarbyl group, X is Si, Ge or Sn, each $R^2$ independently is a leavening group and is F, Cl, Br, I or a sulphonate group optionally being halogen substituted and wherein n is 1, 2 or 3.

47 Claims, No Drawings

PHOSPHORYLATION PROCESS AND CATALYST

CROSS REFERENCE TO RELATED APPLICATIONS

This application is a continuation of application Ser. No. 09/142,846, filed Jan. 4, 1999, now abandoned, which is a 35 USC § 371 application of International Application PCT/SE97/00345, filed Feb. 28, 1997.

The present invention relates to a process and use of at least one Si, Ge or Sn comprising catalyst for phosphorylation, in particular phosphitylation, of hydroxyl groups. A phosphorous compound is added to a hydroxyfunctional compound having at least one hydroxyl group and said addition yields in the presence of said catalyst a phosphorous reaction product having at least one O—P bond.

The manufacture and use of phosphorous compounds, such as phosphates, phosphites and phosphides, are of substantial importance in areas including various animal die, fertilisers, detergents, pharmaceuticals, plasticisers, antioxidants, flame retardants and the like.

Phosphorylation of hydroxyfunctional compounds is known to be performed using phosphorous acids, whereby the phosphorus containing groups react with hydroxyl groups and other similar procedures.

Phosphorylations comprising a reaction between for instance an amide of a phosphorous acid and a hydroxyfunctional compound, as illustrated by the simplified reaction scheme (a) below

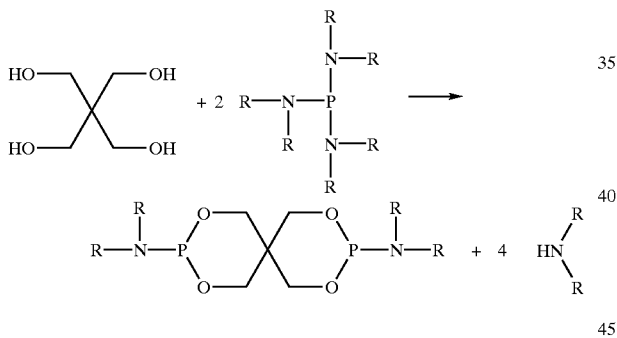

wherein each R independently can be alkyl, cycloalkyl, aryl, alkoxy, cycloalkoxy, aryloxy, thiolo and the like, proceed very slowly and with exceptionally low yield, often as low as 20% or less, and a catalyst is normally used. A frequently used catalyst is tetrazole. derivatives thereof and structural analogues. The yield is thereby increased, but still very low, normally less than 50%. The use of tetrazole and its derivatives as catalysts exhibit, besides the low yield a number of drawbacks such as

- the amount of tetrazole must be optimised in every case,
- excess of tetrazole must be used,
- formation of side products, usually derivatised from disproportionations,
- problems caused by separation, and
- freshly sublimed tetrazole must be used,
- tetrazole is very expensive making large scale syntheses impossible
- tetrazole is difficult, inconvenient and hazardous to handle.

Through the present invention, it has quite unexpectedly been found that a range of compounds, not previously employed as catalysts in phosphitylations and phosphorylations, substantially improve reaction time and yield. The yield is for instance in comparison to tetrazole increased from less than 50% to 80–100%, normally 90–95%.

The present invention refers to a process for phosphorylation, in particular a phosphitylation, of hydroxyl groups and use of at least one Si, Ge or Sn comprising catalyst during said process, whereby a phosphorous compound such as an amide of a trivalent phosphorous acid reacts with a hydroxyfunctional compound yielding a phosphorous reaction product having at least one O—P bond. The process is performed in the presence of at least one catalyst of general formula (1):

$$(R^1)_n X(R^2)_{4-n} \qquad \text{Formula (1)}$$

wherein i) each $R^1$ independently is
  a) hydrogen,
  b) at least one alkanyl, alkenyl, alkynyl, cycloalkanyl, cycloalkanyl, cycloalkynyl, aryl, alkanylaryl, alkenylaryl, alkynylaryl, trityl, alkoxy, cycloalkoxy, aryloxy or amino group,
  c) a polymeric moiety derived from a carbon polymer or copolymer,
  d) at least one halogenated and/or silylated alkanyl, alkeninl, alkynyl cycloalkanyl, cycloalkenyl, cycloalkynyl, aryl, alkanylaryl, alkenylaryl, alkynylaryl, trityl, alkoxy, cycloalkoxy, aryloxy or amino group, and/or
  e) a polymeric moiety derived from a halogenated and/or silylated carbon polymer or copolymer;

ii) X is Si, Ge or Sn;

iii) each $R^2$ independently is a leavening group and is
  a) F, Cl, Br or I; or
  b) a sulphonate group of general formula (2)

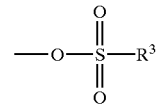

Formula (2)

wherein $R^3$ is F, Cl, Br, I, alkanyl, alkenyl, alkynyl, aryl, arylalkanyl, arylalkenyl, arylalkynyl, haloalkanyl, haloalkenyl, haloalkynyl, haloaryl, haloarylalkanyl, haloarylalkenyl, haloarylalkynyl, arylhaloalkanyl, arylhaloalkenyl, arylhaloalkynyl or a group of formula $CR^4$, wherein $R^4$ is $F_3$, $Cl_3$, $Br_3$ or $I_3$;

iv) n is 1, 2 or 3.

The reaction performed during the process and activated by the compound of Formula (I) can be exemplified by below reaction scheme (b) illustrating the phosphitylation of thymidine using trimethylchlorosilane as catalyst:

Reaction Scheme (b)

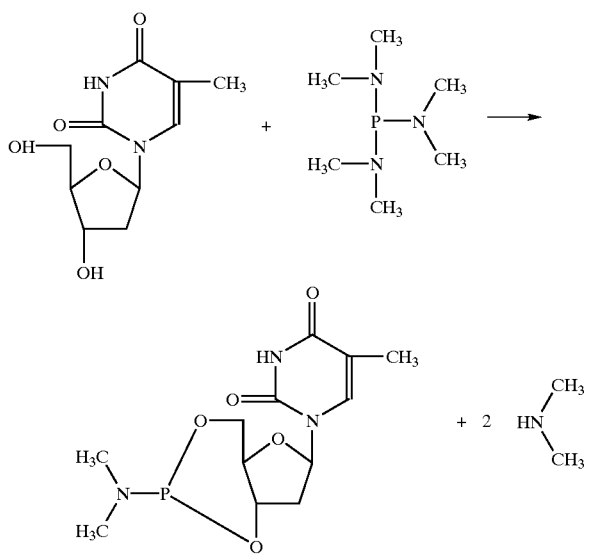

Activation by a catalyst in accordance with the present invention requires normally one equivalent or less. The reaction is fast. often 30 minutes to 2 hours at 20° C., and free of side products. The yield is excellent, in most cases 95–100% and the resulting products are essentially pure requiring no further purification, In preferred embodiments of the invention is each $R^1$ individually methyl, ethyl, butyl, propyl, pentyl, hexyl, heptyl, octal, nonyl, decyl, methylethyl, methylbutyl, methylisobutyl, methylpropyl, methylisopropyl, methyloctyl, methylphenyl, methyltrityl, allylmethyl, allylethyl, ethylbutyl, ethylisobutyl, ethylpropyl, ethylisopropyl, butylphenyl, butylmethoxyphenyl, ethoxy, propoxy, butoxy, ethoxymethyl, ethoxyethyl, thexylmethyl, phenyl, benzyl, xylyl, thexyl, thexylethyl, methyltrityl, butylmethylene, butylphenoxymethyl, methoxymethyl, vinyl, vinylmethyl, vinylethyl, vinylethoxy, cyanomethyl, cyanoethyl, halomethyl, haloethyl, halobutyl, halopropyl, halopentyl, halohexyl, haloheptyl, haloctyl, halononyl, halodecyl, halophenyl, halobenzyl, haloxylyl, halothexyl, methylhalohexyl, halophenylmethyl, butylhalophenylmethyl, halovinyl, vinylhalomethyl or vinylhaloethyl. At least one $R^1$ can in these and other preferred embodiments can be a moiety derived from, for example an analogue of, an organic polymer or copolymer, such as polyethylene, a polystyrene, a polyether or a polyester, or any analogues thereof, which polymer optionally is silylated and/or halogenated. X is in these and other especially preferred embodiments preferably Si.

Employed catalyst is in especially preferred embodiments a trialkylhalosilane, such as a trialkylchlorosilane, trialkyliodosilane, trialkylbromosilane or trialkylfluorosilane preferably selected from the group consisting of trimethylchlorosilane, triethylchlorosilane, tributylchlorosilane, tripropylchlorosilane, trimethyliodosilane, triethyliodosilane, tributyliodosilane, tripropyliodosilane, trimethylbromosilane, triethylbromosilane, tributylbromosilane, tripropylbromosilane, trimethylfluorosilane, triethylfluorosilane, tributylfluorosilane, tripropylfluorosilane.

Further compounds, advantageously being used as catalysts in accordance with the present invention, of Formula (I) wherein X is Si are suitably exemplified by trimethylchlorosilane, trimethylbromosilane, trimethyliodosilane, trimethylsilyltrichloroacetate, trimethylsilyltrifluoroacetate, allyldimethylchlorosilane, bromomethyldimethylchlorosilane, tert-butyldimethylchlorosilane, N-tert-butyldimethylsilyl-N-methyltrifluoroacetamide. N,O-bis(trimethylsilyl) trifluoroacetamide, N-methyl-N-trimethylsilyl-heptafluorobutyramide, N-methyl-N-trimethylsilyltrifluoroacetamide, trimethylsilyltrifluoromethanesulphonate, tert-butyldimethylsilyltrifluoromethanesulphonate, tert-butyldiphenylchlorosilane, tert-butyl-methoxy-phenylbromosilane, chloromethyldimethylchlorosilane, dimethyl(3,3,4,4,5,5,6,6,6-nonafluorohexyl)chlorosilane, dimethylphenylchlorosilane, dimethyltritylbromosilane, diphenylmethylchlorosilane, isopropyldimethylchlorosilane, (pentafluorophenyl) dimethylchlorosilane, thexyldimethylchlorosilane, thexyldimethylsilyl trifluoromethanesulphonate, tributylchlorosilane, triethylchlorosilane, trithylsilyltrifluoromethanesulphonate, triisopropylchlorosilane, triisopropylsilyltrifluoromethanesulphonate, triphenylchlorosilane, tripropylchlorosilane, di-tert-butyldichlorosilane, di-tert-butylsilyl bis (trifluoromethanesulphonate), diethyldichlorosilane, diisopropylsilyl-bis(trifluoromethanesulphonate), dimethyldichlorosilane, diphenyldichlorosilane, methylphenyldichlorosilane, dimethyloctylchlorosilane, dodecyltrichlorosilane, thexyldimethylsilyl-trifluoromethanesulphonate, thexyl-dimethylchlorosilane, trichlorosilan, 3-(triethylsilyl)propyl-trimethylammoniumchloride, trimethylsilylbromoacetate, trimethylsilylchlorosulphonate, 2-(trimethylsilyl) ethoxymethyl chloride, tri(dimethylamino)sulphonium-difluorotrimethylsilicate and 1,3-bis(chloromethyl)-1,1,3,3-tetramethyldisilazane.

One or more solvents are suitably present during the process of the present invention. The solvent is preferably selected from the group consisting of aliphatic solvents, cycloaliphatic solvents, aromatic solvents, 1,3-dioxanes, 1,3-dixolanes, 1,3,5-trioxepanes, furans and/or haloalkanes, such as hexane, toluene, xylene, tetrahydrofuran, dichloromethane and acetonitrile.

The process of the invention and the catalyst used therein are suitable for phosphorylation, in particular phosphitylation, of hydroxyfunctional compounds such as mono, di, tri and polyfunctional alcohols, monosaccharides, disaccharides, polysaccharides, sugar alcohols, cyclodextrins, inositols, nucleosides, terpenoids, lipids, phenols, polyphenols, hydroxyfunctional polymers, hydroxyfunctional carboxyl, acids and/or derivatives of said hydroxyfunctional compounds. The hydroxyfunctional compound is advantageously selected from the group consisting of:

a) pentoses, hexoses and heptoses such as D/L-ribose, D/L-arabinose. D/L-xylose, D/L-lyxose, D/L-allose, D/L-altrose, D/L-alucose, D/L-mannose, D/L-gulose, D/L-idose, D/L-galactose, D/L-talose, D/L-glucoheptose. D/L-mannoheptose, D/L-ribulose, D/L-xylulose D/L-psicose, D/L-fructose, D/L-sorbose, D/L-tagatose, D/L-sedoheptulose and/or derivatives of said pentoses, hexoses and heptoses, b) pentitols, hexitols and heptitols such as D/L-ribitol, D/L-arabinitol, D/L-xylitol, D/L-lyxitol, D/L-allitol, D/L-altritol, D/L-glucitol, D/L-mannitol, D/L-gulitol, D/L- iditol, D/L-galactitol, D/L-talitol, D/L-glucoheptitol, D/L-mannoheptitol, D/L-ribulitol, D/L-xylulitol, D/L-psicitol, D/L-fructitol, D/L-tagatitol, D/L-sedoheptulitol and derivatives of said pentitols, hexitols and heptitols, c) anhydropentitols, anhydrohexitols, anhydroheptitols and derivatives thereof, d) celobioge, maltose, lactose, saccharose, gentobiose, melibiose, trehalose, turanose and derivatives thereof, e) starch, glycogen, cellulose, dextran, tunicine and/or derivatives thereof, and f) myo-inositol, cis-inositol, epi-inositol, allo-inositol, neo-inositol, muco-inositol, D/L-chiro-inositol, scyllo-inositol and derivatives of said inositols, g) 5-ethyl-5-methanol-1,3-dioxane, 2-ethyl-2-butyl-1,3-propanediol, neopentyl glycol, glycerol, trimethylolpropane, trimethylolethane, pentaerythritol, diglycerol, ditrimethylolpropane, ditrimethylolethane, dipentaerythritol, tripentaerythritol and derivatives thereof, h) 2,2-dimethylolpropionic acid, α,α-bis-(hydroxymethyl) butyric acid, α,α,α-tris(hydroxymethyl)acetic acid, α,α-bis-(hydroxymethyl)valeric acid, α,α-bis(hydroxy) propionic acid, 3,5-dihydroxybenzoic acid, α,β-dihydroxypropionic acid, heptonic acid, citric acid, tartaric acid, dihydroxymaloic acid, gluconic acid and derivatives thereof.

As used herein, the term "D/L" is used to indicate the various isomers of the particular compound, including any mixture thereof. For example, "D/L-ribose" denotes D-ribose, L-ribose or any combination thereof, including the racemic mixture.

The hydroxyfunctional compound can also suitably be a dendritic or hyperbranched macromolecule. Hyperbranched and dendritic macromolecules normally consist of an initiator or nucleus having one or more reactive sites and a number of surrounding branching layers optionally being chain terminated. The layers are usually called generations, whereby each generation comprises one or more branches, usually called dendrons. A macromolecule suitable for a phosphitylation according to the present invention can be composed of a monomeric or polymeric nucleus to which 1–100, preferably 1–20, generations consisting of at least one monomeric or polymeric chain extender are added. The chain extender has at least one, preferably at least two, reactive hydroxyl groups and at least one reactive carboxyl group. The terminal functions of yielded macromolecule is, prior to the optional chain termination, substantially hydroxyl groups. An optional chain termination is performed in such a manner and to such a degree that the macromolecule finally has at least one terminal hydroxyl group. The nucleus may be a compound, such as an alcohol, a polyalcohol, a glycidyl ester, a glycidyl ether or the like having at least one reactive hydroxyl or epoxide group. In further embodiments, the nucleus may be a metal ion or an organometallic compound being hydroxy and/or epoxide functional or the like.

Hyperbranched and dendritic macromolecules (dendrimers) can generally be described as three dimensional highly branched molecules having a tree-like structure. Dendrimers are highly symmetric, while similar macromolecules designated as hyperbranched may to a certain degree hold an asymmetry, yet maintaining the highly branched tree-like structure. Dendrimers can be said to be monodisperse variations of hyperbranched macromolecules. The composition of hyperbranched dendritic or near dendritic macromolecule can be illustrated by below simplified Formula (3.1) and (3.2) illustration a hyperbranched macromolecule (Formula 3.1) and a dendron (Formula 3.2) being part of the macromolecule. Regard is not taken to any three dimensional structure. The macromolecule has two generations of chain extenders (A and B) having 3 and 4 reactive sites. The reactive sites are one carboxyl group, reacted with the nucleus (Y), and hydroxyl groups. The macromolecule is partly chain terminated by means of a chain terminator (T). The nucleus or initiator (Y) is as previously defined.

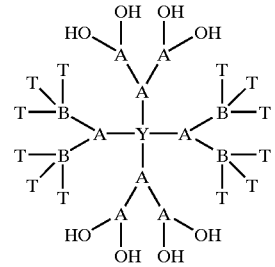

Formula 3.1

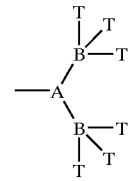

Formula 3.2

The hydroxyfunctional compound can, furthermore, be a dendron of for instance general formula (4) $R^{12}(OOR^{13})_q(OOR^{14})_y(OOR^{15})_z$, wherein each $R^{12}$, $R^{13}$, $R^{14}$ and $R^{15}$ independently is alkanyl, alkenyl, alkynyl, cycloalkanyl, cycloalkenyl, cycloalkynyl, aryl, alkanylaryl, alkenylaryl or alkynylaryl, q is an integer and at least 1, y is 0 or an integer and at least 1 and wherein z is an integer between 1 and 25, preferably between 1 and 10. A suitable dendron can be exemplified by self condensated 2,2-dimethylolpropionic acid, whereby a suitable number of moles of said compound is condensated (esterified) at a temperature of for instance 150–25°C. 2,2-Dimethylolpropionic acid has two hydroxyl groups and one carboxyl group and one molecule of the compound can thus react with two other molecules, whereby a highly branched chain consisting of esterified 2,2-dimethylolpropionic can be prepared.

The phosphorous compound used in the phosphorylation process is advantageously an amide of a phosphorous acid containing trivalent phosphorus, which compound is of general formula (5), (6) or (7), $R^5R^6PNR^7R^8$, $R^6P(NR^7R^8)_2$ or $P(NR^7R^8)_3$, wherein each $R^5$ and $R^6$ independently is an alkyl, a cycloalkyl, an aryl, an alkoxy, a cycloalkoxy, an aryloxy, a thiolo or an amido group and wherein each $R^7$ and $R^8$ independently is an alkyl, a cycloalkyl or an aryl group. The phosphorous compound can alternatively be of general formula (8) or (9), $(R^9CH_2O)_2PNR^{10}R^{11}$ or $(NCCH_2CH_2O)_2PNR^{10}R^{11}$, wherein each $R^9$ independently is aryl or alkaryl and wherein each $R^{10}$ and $R^{11}$ independently are $C_1$–$C_{12}$ alkyl. Said phosphorous compounds can be exemplified by neopentylene-N,N-dimethylphosphoroamidite, o-phenylene-N,N-diisopropylphosphoroamidite, di-(2-cyanoethyl)-N,N-diisopropylphosphoroamidite, 2-cyanoethyl-N,N-diisopropylfluorophosporoamidite, dibenzyl-N,N-diethylphosphoroamidite and hexamethylphosphorotriamide.

A phosphitylation process according to the present invention is preferably perform, at a temperature of −80° C. to 120° C. such as −10° C. to 80° C. or 0° C. to 40° C., using a catalyst amount corresponding to 0.01 to 3, preferably 0.05 to 1 and most preferably 0.1 to 0.5, equivalents calculated on phosphorous equivalents. The amount of catalyst is normally between 5% and 80%. A suitable and preferred order of addition is 1 the phosphorous compound or compounds, 2 the hydroxyfunctional compound or compounds and 3 the catalyst or catalysts The phosphorylated, in particular phosphitylated, reaction product obtained in the process and by using the catalyst of the present invention can optionally be further processed. Trivalent phosphorus included in the reaction product can for example be oxidised to pentavalent phosphorus using an oxidising agent, such as a peroxide, a hydroperoxide, a peracid, or by means of sulphur transferring reagents including elemental sulphur. Phosphites can thus be transformed into phosphates yielding for instance pharmaceutically active and important trisphosphates of monosaccharides and inositols. Furthermore, β-cyanoalkyl groups included in the phosphorylated product can be eliminated in the presence of a base, such as potassium hydroxide, sodium hydroxide or an amine and benzyl groups by means of a hydrogenolysis.

The present invention makes it possible to employ simple phosphitylation reagents of for instance formula (8) or (9) for phosphitylation of 3'-protected nucleosides, 5'-protected nucleosides and other alcoholic compounds of biological importance, such as sugars, terpenoids and lipids. Oxidisation of phosphites to phosphates, optional removal of β-cyanoalkyl and benzyl groups, result in a phosphate yield of normally more than 90%.

Further application areas of the process of present invention and catalyst used therein are preparation of oligomeric and polymeric dendrons from polyols by a suitable choice of phosphitylation reagent, preparation of antioxidants containing a nucleus of trivalent phosphorus, preparation of intermediates containing trivalent phosphorus, which can be converted into tetravalent or pentavalent structures resulting in important biophosphates and their structural analogues as well as material improving components, such as plasticisers and flame retardants, preparation of olefinic monomers containing trivalent and pentavalent phosphorus, which monomers when heated in the presence of for instance benzoyl peroxide give flame retardant solids. and preparation of detergents.

These and other objects and the attendant advantages will be more fully understood from the following detailed description, taken in conjunction with embodiment Examples 1–11, whereby said Examples present:

Example 1: Phosphitylation of uridine—Comparison between (i) no catalyst, (ii) tetrazole and (iii) catalyst according to the present invention.

Example 2: Synthesis of ethyl neopentylene phosphite.

Example 3: Synthesis of ethyl o-phenylene phosphite.

Example 4: Synthesis of thymidine cyclic 3',5'-N,N-dimethylphosphoroamidite.

Example 5: Synthesis of (±) 2,3,6-tri-O-benzyl-myo-inositol-1,4,5-tris[di-(2-cyanoethyl) phosphite].

Example 6: Synthesis of α-methyl-6-O-acetyl-D-mannopyranoside-2,3,4-tris-(dibenzyl phosphite).

Example 7: Synthesis of (±) 3,4,5,6-tetra-O-benzyl-myo-inositol-1,2-bis(di-benzyl phosphite).

Example 8: Synthesis of (±) 3,4,5-tri-O-benzyl-myo-inositol-1,2,6-O-tris(di-benzyl phosphite).

Example 9: Synthesis of (±) 3,4,5,6-tetra-O-benzyl-myo-inositol-1,2-bis(2-cyanoethyl fluorophosphite).

Example 10: Oxidization the phosphite of Example 6 yielding corresponding phosphate.

Example 11: Elimination of benzyl groups in included in the phosphate of Example 10.

EXAMPLE 1

Phosphitylation of Thymidine According to the Following Reaction Scheme

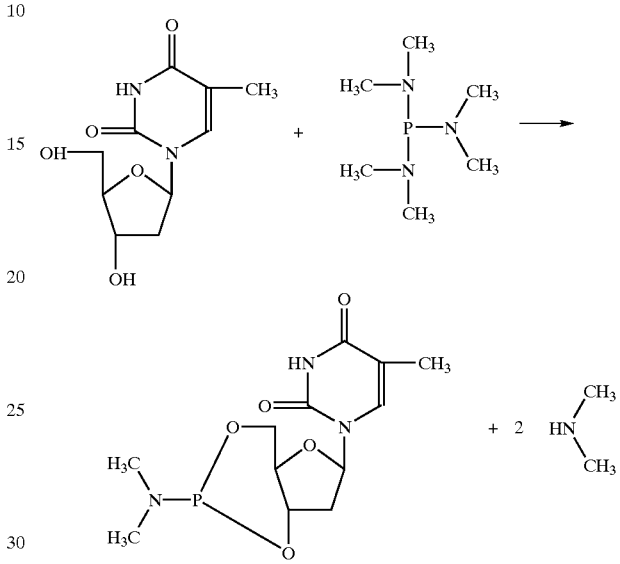

was repeatedly performed using i) no catalyst, dioxane as solvent and 80° C. as reaction temperature, ii) a 6 fold excess of tetrazole (calculated on P) as catalyst, dioxane as solvent and 80° C. as reaction temperature, iii) 0.2 5 equivalent of triethylchlorosilane (calculated on P) as catalyst, dioxane as solvent and 20° C. as reaction temperature, giving the following average yield of cyclic amidite i) ≈20% after 8 hours of reaction, ii) 25–30% after 6 hours of reaction iii) >95% after 2 hours of reaction, whereby i) and ii) are comparative phosphitylations outside the scope of the invention and iii) is a phosphitylation in accordance with the invention.

Above result clearly shows the great advantages obtained when using a phosphitylation process according to the present invention, such as a substantially increased yield, reduced amount of catalyst, reduced reaction temperature and time, reduced cost, and improved environmental and handling safety

EXAMPLE 2

34.5 g (0.2 mole) of neopentylene-N,N-dimethylphosphoroamidite, 9.7 g (0.21 mole) of ethanol and 150 ml sodium dried tetrahydrofuran were charged in a 4-necked reaction flask equipped with a stirrer, a thermometer, an instillation funnel and an inlet for inert gas. The mixture was stirred and allowed to form a solution to which 5.4 g (0.05 mole) trimethylchlorosilane was instilled at such a rate that the temperature never exceeded 20° C. Stirring was maintained during the instillation and cooling of the reaction flask was applied if necessary. The reaction mixture was stirred and kept at 20° C. for a further 30 minutes. Solvent, excess of ethanol and unchanged trimethylchlorosilane were now removed in vacuo. The residue was vacuum distilled to give 30.4 g of ethyl neopentylene phosphite: Yield 85%; $Bp_{16}$ 77–78° C.; $n_D^{20}$: 1.4437.

All operations were, in order to secure a high yield and product purity, performed under a blanket of nitrogen free of oxygen and moisture.

EXAMPLE 3

47.8 g (0.2 mole) of o-phenylene-N,N-diisopropylphosphoroamidite, 9.7 g (0.21 mole) of ethanol and 150 ml sodium dried tetrahydrofuran were charged in a 4-necked reaction flask equipped with a stirrer, a thermometer, an instillation funnel and an inlet for inert gas. The mixture was stirred and allowed to form a solution to which 5.4 g (0.05 mole) trimethylchlorosilane was instilled at such a rate that the temperature never exceeded 20° C. Stirring was maintained during the instillation and cooling of the reaction flask was applied if necessary. The reaction mixture was stirred and kept at 20° C. for a further 30 minutes. Solvent, excess of ethanol and unchanged trimethylchlorosilane were now removed in vacuo and 35.0 g of ethyl o-phenylene phosphite. Analysis indicated that obtained product had a purity of at least 96% Yield 95%; $^{31}$P NMR δ: −129 ppm (neat); $n_D^{20}$: −1.4437.

All operations were, in order to secure a high yield and product purity, performed under a blanket of nitrogen free of oxygen and moisture.

EXAMPLE 4

20 ml of sodium dried tetrahydrofuran was charged in a 50 ml flask (dried at 300° C.) equipped with a magnetic stirrer and filled with dry oxygen free argon. The flask was covered with a rubber septum and 0.134 (0.83 mmole) of hexamethylphosphorotriamide and 0.076 g (0.83 mmole) of trimethylchlorosilane were added at 20° C. and stirred. 0.2 g (0.83 mmole) of thymidine was after 5 minutes of stirring added at 20° C. and the reaction mixture was stirred at 20° C. for a further 60 minutes. Solvent and catalyst were now evaporated in vacuo and 0.3 g (yield 98%) of crude thymidine cyclic 3',5'-dimethylphosphoroamidite was obtained. The crude product was dissolved in 5 ml of $CH_2Cl_2$ and purified by column chromatography on silica gel using $CH_2Cl_2/CH_3COCH_3$ 10:3 as eluent. The purification resulted in 0.28 g of pure thymidine cyclic 3',5'-dimethylphosphoroamidite: Yield 95%, $^{31}$P NMR ($C_6D_6$) δ: 138.27, 137.91.

EXAMPLE 5

20 ml of sodium dried tetrahydrofuran was charged in a 50 ml flask (dried at 300° C.) equipped with a magnetic stirrer and filled with dry oxygen free argon. The flask was covered with a rubber septum and 3 mmole of di-(2-cyanoethyl)-N,N-diisopropylphosphoroamidite and 3 mmole of trimethylchlorosilane were added at 20° C. and stirred. A solution of 1 mmole of (±) 1,2,4-tri-O-benzyl-myo-inositol in 10 ml of sodium dried tetrahydrofuran was after 5 minutes of stirring added at 20° C. and the reaction mixture was stirred at 20° C. for a further 2 hours. Solvent and catalyst were now evaporated in vacuo, yielding crude (±) 2,3,6-tri-O-benzyl-myo-inositol-1,4,5-tris[di-(2-cyanoethyl)phosphite): Yield 95%, $^{31}$P NMR (CDCl$_3$) δ: 139.6; 137.91, P-1, 140.2, 141.0, P-4, ($^5J_{pp}$=3.4 Hz).

EXAMPLE 6

20 ml of sodium dried tetrahydrofuran was charged in a 50 ml flask (dried at 300° C.) equipped with a magnetic stirrer and filled with dry oxygen free argon. The flask was covered with a rubber septum and 3 mmole of dibenzyl-N, N-diethylphosphoroamidite and 0.05 mmole of trimethylchlorosilane were added at 20° C. and stirred A solution of 1 mmole of α-methyl-6-O-acetyl-D-mannopyranoside in 10 ml of sodium dried tetrahydrofuran was after 5 minutes of stirring added at 20° C. and the reaction mixture was stirred at 20° C. for a further 2 hours. Solvent and catalyst were now evaporated in vacuo. The residue was purified by column chromatography on silica gel 60 (230–400 mesh) using hexane/dietylether as eluent. The purification resulted in 0.8 g of pure α-methyl-6-O-acetyl-D-mannopyranoside-2,3,4-tris(dibenzylphosphite): Yield 89%; $^{31}$P NMR ($C_6D_6$) δ: 140.3, 141.6 (2P).

EXAMPLE 7

20 ml of sodium dried tetrahydrofuran was charged in a 50 ml flask (dried at 300° C.) equipped with a magnetic stirrer and filled with dry oxygen free argon. The flask was covered with a rubber septum and 2 mmole of dibenzyl-N, N-diethylphosphoroamidite and 2 mmole of trimethylchlorosilane were added at 20° C. and stirred. A solution of 1 mmole of (±) 3,4,5,6-tetra-O-benzyl-myo-inositol in 10 ml of sodium dried tetrahydrofuran was after 5 minutes of stirring added at 20° C. and the reaction mixture was stirred at 20° C. for a further 2 hours. Solvent and catalyst were now evaporated in vacuo. The residue was purified by column chromatography on silica gel 60 (230–400 mesh) using hexane/diethylether 8:1 as eluent. The purification resulted in 0.82 g of pure (±) 3,4,5,6-tetra-O-benzyl-myo-inositol-1, 2-bis(dibenzylphosphite): Yield 80%, $^{31}$P NMR ($C_6D_6$) δ: 140.5 (d, J=1.8 Hz), 140.6 (d, J=1.8 Hz).

EXAMPLE 8

20 ml of sodium dried tetrahydrofuran was charged in a 50 ml flask (dried at 300° C.) equipped with a magnetic stirrer and filled with dry oxygen free argon. The flask was covered with a rubber septum and 3 mmole of dibenzyl-N, N-diethylphosphoroamidite and 3 mmole of trimethylchlorosilane were added at 20° C. and stirred. A solution of 1 mmole of (±) 3,4,5-tri-O-benzyl-myo-inositol in 10 ml of sodium dried tetrahydrofuran was after 5 minutes of stirring added at 20° C. and the reaction mixture was stirred at 20° C. for a further 2 hours. Solvent and catalyst were now evaporated in vacuo. The residue was purified by column chromatography on silica gel 60 (230–400 mesh) using hexane/diethylether 5:1 as eluent. The purification resulted in 1.2 g of pure (±) 3,4,5-tri-O-benzyl-myo-inositol-1,2,6-tris(dibenzylphosphite): Yield 100%; $^{31}$P NMR ($C_6D_6$) δ: 140.2 (d, $J_{P1P2}$ 2.1 Hz), 140.8 (dd, $J_{P1P2}$ 2.1 Hz, $J_{P1P6}$ 3.9 Hz, P-1), 143.2 (d, $J_{P1P6}$ 3.9 Hz, P-6).

EXAMPLE 9

20 ml of sodium dried tetrahydrofuran was charged in a 50 ml flask (dried at 300° C.) equipped with a magnetic stirrer and filled with dry oxygen free argon. The flask was covered with a rubber septum and 0.86 mmole of 2-cyanoethyl-N,N-diisopropylfluorophosphoroamidite and 0.86 mmole of trimethylchlorosilane were added at 20° C.

and stirred. A solution of 0.4 mmole of (±) 3,4,5.6-tetra-O-benzyl-myo-inositol in 10 ml of sodium dried tetrahydrofuran was after 5 minutes of stirring added at 20° C. and the reaction mixture was stirred at 20° C. for a further 2 hours. Solvent and catalyst were now evaporated in vacuo. The residue was purified by column chromatography on silica gel 60 (230–400 mesh) using $CH_2Cl_2/CH_3COCH_3$ 10:3 as eluent. The purification resulted in 0.23 g of pure (±) 3,4,5,6-tetra-O-benzyl-myo-inositol-1,2-bis(2-cyanoethylphosphite) Yield 80%, $^{31}P$ NMR ($CDCl_3$) δ: 138.6 m, 123.6 m.

EXAMPLE 10

0.50 g of α-methyl-6-O-acetyl-D-mannopyranoside-2,3,4-tris(dibenzylphosphite), obtained in Example 6, was dissolved in 20 ml of dichloromethane. 0.97 g of m-chloroperbenzoic acid in 20 ml of dichloromethane was now instilled during 1 hour. The temperature was adjusted to 20° C. and maintained for a further 1.5 hour followed by an evaporation of the solvent. The residue was by NMR identified to be α-methyl-6-O-acetyl-D-mannopyranoside-2,3,4-tris(dibenzylphosphate).

EXAMPLE 11

0.35 g of α-methyl-6-O-acetyl-D-mannopyranoside-2,3,4-tris(dibenzylphosphate), obtained in Example 10, was dissolved in 5 ml of ethanol and hydrogenated for 10 minutes at 1 bar and 20° C. over 0.10 g of 5% Pd/C. The mixture was evaporated and the residue was by NMR identified to be α-methyl-6-O-acetyl-D-mannopyranoside-2,3,4-trisphosphate.

While particular embodiments of the invention have been shown, it will be understood, of course, that the invention is not limited thereto since many modifications may be made, and it is, therefore, contemplated to cover by the appended claims any such modifications as fall within the true spirit and scope of the invention.

What is claimed is:

1. A process for phosphorylation of a hydroxyfunctional compound having one or more hydroxyl group substituents by phosphitylation followed by oxidation comprising addition of a phosphitylation reagent or phosphorous compound to a hydroxyfunctional compound having at least one hydroxyl group which addition yields a product having at least one O—P bond wherein said phosphorylation is performed in the presence of at least one catalyst of general formula $(R^1)_nX(R^2)_{4-n}$ wherein
   i) each $R^1$ independently is
      a) at least one alkyl, alkenyl, alkynyl, cycloalkyl, cycloalkenyl, cycloaliknyl, aryl, alkylaryl, alkenylaryl, alkynylaryl, trityl, alkoxy, cycloalkoxy, or aryloxy,
      b) a polymeric moiety selected from the group consisting of organic polymer, copolymer and analogues thereof,
      c) at least one halogenated and/or silylated alkanyl, alkenyl, alkyl, cycloalkanyl, cycloalkenyl, cycloalkynyl, aryl, alkanylaryl, alkenylaryl, alkynylaryl, trityl, alkoxy, cycloalkoxy, aryloxy or amino group, or
      d) a polymeric moiety derived from a compound selected from the group consisting of a halogenated organic polymer, a halogenated organic copolymer, a silylated organic polymer, a silylated organic copolymer, a mixture of silylated and halogenated organic polymers, a mixture of silylated and halogenated organic copolymers, and analogues thereof;

ii) X is Si;
   iii) each $R^2$ independently is a leaving group and is
      a) F, Cl, Br or I; or
      b) a sulphonate group of formula

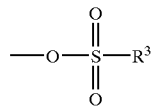

wherein $R^3$ is F, Cl, Br, I, alkyl, alkenyl, alkynyl, aryl, arylalkanyl, arylalkenyl, arylalkynyl, haloalkanyl, haloalkenyl, haloalkynyl, haloaryl, haloarylalkanyl, haloarylalkenyl, haloarylalkynyl, arylhaloalkanyl, arylhaloalkenyl, arylhaloalkynyl or a group of formula $R^4$ wherein $R^4$ is selected from the group consisting of $CF_3$, $CCl_3$, $CBr_3$ and $CI_3$, and
   iv) n is 1, 2 or 3.

2. A process according to claim 1, wherein each $R^1$ individually is selected from the group consisting of methyl, ethyl, butyl, propyl, pentyl, hexyl, heptyl, octyl, nonyl, decyl, methylethyl, methylbutyl, methylisobutyl, methylpropyl, methylisopropyl, methyloctyl, methylphenyl, methyltrityl, allylmethyl, allylethyl, ethylbutyl, ethylisobutyl, ethylpropyl, ethylisopropyl, butylphenyl, butylmethoxyphenyl, ethoxy, propoxy, butoxy, ethoxymethyl, ethoxyethyl, thexylmethyl, phenyl, benzyl, xylyl, thexyl, thexylethyl, methyltrityl, butylmethylene, butylphenoxymethyl, methoxymethyl, vinyl, vinylmethyl, vinyl ethyl, vinylethoxy, cyanomethyl, cyanoethyl, halomethyl, halo ethyl, halobutyl, halopropyl, halopentyl, halohexyl, haloheptyl, haloctyl, halononyl, halodecyl, halophenyl, halobenzyl, haloxylyl, halothexyl, methylhalohexyl, halophenylmethyl, butylhalophenylmethyl, halovinyl, vinylhalomethyl and vinylhaloethyl.

3. A process according to claim 1, wherein at least one $R^1$ is an analogue of a polymer or copolymer.

4. A process according to claim 3, wherein said polymer is silylated and/or halogenated.

5. A process according to claim 1, wherein at least one $R^1$ is a moiety derived from a polymer or copolymer, selected from the group consisting of polyethylene, polystyrene, polyether and polyester.

6. A process according to claim 1, wherein the catalyst is a trialkylhalosilane.

7. A process according to claim 6 wherein the trialkylhalosilane is selected from the group consisting of trialkylchlorosilane, trialkyliodosilane, trialkyl bromosilane and trialkylfluorosilane.

8. A process according to claim 6, wherein the catalyst is selected from the group consisting of trimethylchlorosilane, triethylchlorosilane, tributylchlorosilane, tripropylchlorosilane, trimethyliodosilane, triethyliodosilane, tributyl iodosilane, tripropyliodosilane, trimethylbromosilane, triethylbromosilane, tributylbromosilane, tripropylbromosilane, trimethylfluorosilane, triethyl fluorosilane, tributylfluorosilane, and tripropylfluorosilane.

9. A process according to claim 1, wherein at least one solvent is present during said phosphitylation.

10. A process according to claim 9 wherein the solvent is one or more selected from the group consisting of aliphatic solvent, cycloaliphatic solvent, aromatic solvent, 1,3-dioxane, 1,3-dioxolane, 1,3,5-trioxepane, furan and haloalkane.

11. A process according to claim 10, wherein the solvent is at least one compound selected from the group consisting of hexane, toluene, xylene, tetrahydrofuran, dichloromethane and acetonitrile.

12. A process according to claim 1, wherein the hydroxyfunctional compound is at least one selected from the group consisting of an alcohol, a polyalcohol, a monosaccharide, a disaccharide, a polysaccharide, a sugar alcohol, a cyclodextrin, an inositol, a nucleoside, a terpenoid, a lipid, a phenol, a polyphenol, a hydroxyfinctional hyperbranched macromolecule, a hydroxyfunctional polymer, a hydroxyfunctional carboxylic acid, a analogues of said hydroxyfunctional compounds, and combinations thereof.

13. A process according to claim 12, wherein the hydroxyfunctional compound is selected from the group consisting of pentose, hexose, and heptose, wherein the heptose is at least one selected from the group consisting of D/L-ribose, D/L-arabinose, D/L-xylose, D/L-lyxose, D/L-allose, D/L-altrose, D/L-glucose, D/L-mannose, D/L-gulose, D/L-idose, D/L-galactose, D/L-talose, D/L-glucoheptose, D/L-mannoheptose, D/L-ribulose, D/L-xylulose, D/L-psicose, D/L-fructose, D/L-sorbose, D/L-tagatose, D/L-sedoheptulose and analogues of said pentoses, hexoses or heptoses.

14. A process according to claim 12, wherein the hydroxyfunctional compound is selected from the group consisting of pentitol, hexitol and heptitol, wherein the heptitol is at least one selected from the group consisting of D/L-ribitol, D/L-arabinitol, D/L-xylitol, D/L-lyxitol, D/L-allitol, D/L-altritol, D/L-glucitol, D/L-mannitol, D/L-gulitol, D/L-iditol, D/L-galactitol, D/L-talitol, D/L-glucoheptitol, D/L-mannoheptitol, D/L-ribulitol, D/L-xylulitol, D/L-psicitol, D/L-fructitol, D/L-tagatitol, D/L-sedohaptulitol and analogues of said pentitols, hexitols or heptitols.

15. A process according to claim 14, wherein said pentitols, hexitols and heptitols are at least one selected from group consisting of the anhydropentitols, anhydrohexitols, anhydroheptitols and analogues thereof.

16. A process according to claim 12, wherein the hydroxyfunctional compound is at least one inositol selected from the group consisting of myo-inositol, cis-inositol, epi-inositol, allo-inositol, neo-inositol, muco-inositol, D/L-chiro-inositol, scyllo-inositol and analogues thereof.

17. A process according to claim 12, wherein the hydroxyfunctional compound is selected from the group consisting of mono, di, tri and polyfunctional alcohols.

18. A process according to claim 12, wherein the hydroxyfunctional compound comprises a hydroxyfunctional acid.

19. A process according to claim 12, wherein the hydroxyfunctional compound is a hyperbranched macromolecule comprising a monomeric or polymeric nucleus having at least one reactive epoxide or hydroxyl group to which 1–100 generations of at least one monomeric or polymeric chain extender having at least one reactive hydroxyl group and at least one reactive carboxyl group and that terminal functions of said macromolecule consist essentially of hydroxyl groups.

20. A process according to claim 19, wherein the hyperbranched macromolecule is partly chain terminated and that said macromolecule has at least one terminal function being a hydroxyl group.

21. A process according to claim 1, wherein the phosphorous compound is an amide of a phosphorous acid containing trivalent phosphorus, which compound is of general formula $R^6P(NR^7R^8)_2$ or $P(NR^7R^8)_3$, wherein each $R^7$ and $R^8$ independently is selected from the group consisting of alkyl, cycloalkyl, aryl, alkoxy, cycloalkoxy, aryloxy, a thio, and an amido group having a point of attachment at the carbon, and wherein each $R^7$ and $R^8$ independently is selected from the group consisting of an alkyl, a cycloalkyl and an aryl group wherein $R^6$ is an alkyl, a cycloalkyl, an aryl, an alkoxy, a cycloalkoxy, an aryloxy, a thiolo, or an amido group.

22. A process according to claim 1, wherein the phosphorous compound is of general formula $(R^9CH_2O)_2PNR^{10}R^{11}$ or $(NCCH_2CH_2O)_2PNR^{10}R^{11}$, wherein each $R^9$ independently selected from the group consisting of aryl and alkaryl and wherein each $R^{10}$ and $R^{11}$ independently are $C_1$–$C_{12}$ alkyl.

23. A process according to claim 22, wherein the phosphorous compound is selected from the group consisting of neopentylene-N,N-dimethylphosphoramidite, o-phenylene-N,N-diisopropyl phosphoramidite, di-(2-cyanoethyl)-N,N-diisopropylphosphoramidite, dibenzyl-N,N-diethyl phosphoramidite and hexamethylphosphorotriamide.

24. A process according to claim 1, wherein said process is performed at a temperature of −80° C. to 120° C.

25. A process according claim 1, wherein the catalyst is present in an amount corresponding to 0.01 to 3 equivalents calculated on phosphorous equivalents.

26. A process according to claim 1, wherein elimination of any cyanoalkyl group or groups included in yielded phosphorous reaction product is performed in presence of a base, the base being selected from the group consisting of potassium hydroxide, sodium hydroxide and amine.

27. A process according to claim 1, wherein elimination of any benzyl group or groups present in yielded phosphorous reaction product is performed by means of a hydrogenolysis.

28. A process according to claim 1, wherein the oxidation is performed using at least one oxidizing agent by means of a sulphur transferring reagent.

29. A process according to claim 1, wherein the phosphite is a trisphosphite of a compound selected from the group consisting of a monosaccharide, a sugar alcohol and an inositol yielding corresponding trisphosphate.

30. A catalyst for a process of phosphitylation of general formula $(R^1)_nX(R^2)_{4-n}$ wherein i) each $R^1$ independently is
  a) at least one alkanyl, alkenyl, alkynyl, cycloalkl, cycloalkenyl, cycloalkynyl, aryl, alkylaryl, alkenylaryl, alkynylaryl, trityl, alkoxy, cycloalkoxy, or aryloxy,
  b) a polymeric moiety derived from an organic polymer or copolymer,
  c) at least one halogenated and/or silylated alkyl, alkenyl, alkynyl, cycloalkyl, cycloalkenyl, cycloalkynyl, aryl, alkanylaryl, alkenylaryl, alkynylaryl trityl, alkoxy, cycloalkoxy, or aryloxy,
  d) a polymeric moiety selected from the group consisting of halogenated and silylated organic polymer or copolymers and analogues thereof;
ii) X is Si;
iii) each $R^2$ independently is a leaving group and is
  a) F, Cl, Br or I; or
  b) a sulphonate group of formula

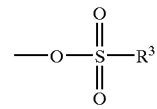

wherein $R^3$ is F, Cl, Br, I, alkyl, alkenyl, alkynyl, aryl, arylalkyl, arylalkenyl, arylalkynyl, haloalkanyl, haloalkenyl, haloalkynyl, haloaryl, haloarylalkanyl, haloarylalkenyl, haloarylalkynyl, arylhaloalkanyl, arylhaloalkenyl, arylhaloalkynyl or a group of formula $R^4$, wherein $R^4$ is selected from the group consisting of $CF_3$, $CCl_3$, $CBr_3$ and $CI_3$; and iv) n is 1, 2 or 3.

31. A catalyst for a process of phosphitylation according to claim 30, wherein each $R^1$ individually is selected from the group consisting of methyl, ethyl, butyl, propyl, pentyl, hexyl, heptyl, octyl, nonyl, decyl, methylethyl, methylbutyl, methylisobutyl, methylpropyl, methylisopropyl, methyloctyl, methylphenyl, methyltrityl, allylmethyl, allylethyl, ethylbutyl, ethylisobutyl, ethylpropyl, ethylisopropyl, butylphenyl, butylmethoxyphenyl, ethoxy, propoxy, butoxy, ethoxymethyl, ethoxyethyl, thexylmethyl, phenyl, benzyl, xylyl, thexyl, thexylethyl, methyltrityl, butylmethylene, butylphenoxymethyl, methoxymethyl, vinyl, vinylmethyl, vinylethyl, vinylethoxy, cyanomethyl, cyanoethyl, halomethyl, haloethyl, halobutyl, halopropyl, halopentyl, halohexyl, haloheptyl, halooctyl, halononyl, halodecyl, halophenyl, halobenzyl, haloxylyl, halothexyl, methylhalohexyl, halophenylmethyl, butylhalophenylmethyl, halovinyl, vinylhalomethyl and vinylhaloethyl.

32. A catalyst for a process of phosphitylation according to claim 30, wherein at least one $R^1$ is a moiety derived from a polymer or copolymer, selected from the group consisting of polystyrene, polyether and polyester.

33. A catalyst for a process of phosphitylation according to claim 32, wherein said polymer is silylated and/or halogenated.

34. A catalyst for a process of phosphitylation according to claim 30, wherein the catalyst is a trialkylhalosilane.

35. A catalyst for a process of phosphitylation according to claim 34 wherein the trialkylhalosilane is selected from the group consisting of trialkylchlorosilane, trialkyliodosilane, trialkyl bromosilane and trialkylfluorosilane.

36. A catalyst for a process of phosphitylation according to claim 34, wherein the catalyst is selected from the group consisting of trimethylchlorosilane, triethylchlorosilane, tributylchlorosilane, tripropylchlorosilane, trimethyliodosilane, triethyliodosilane, tributyl iodosilane, tripropyliodosilane, trimethylbromosilane, triethylbromosilane, tributylbromosilane, tripropylbromosilane, trimethylfluorosilane, triethyl fluorosilane, tributylfluorosilane, and tripropylfluorosilane.

37. A process according to claim 7 wherein the catalyst is trimethylchlorosilane, triethylchlorosilane, tributylchlorosilane, tripropylchlorosilane, trimethyliodosilane, triethyliodosilane, tributyl iodosilane, tripropyliodosilane, trimethylbromosilane, triethylbromosilane, tributylbromosilane, tripropylbromosilane, trimethylfluorosilane, triethyl fluorosilane, tributylfluorosilane, tripropylfluorosilane.

38. A process according to claim 12, wherein the hydroxy-finctional compound is a hyperbranched macromolecule composed of a monomeric or polymeric nucleus having at least one-reactive epoxide or hydroxyl group to which 1–20 generations of at least one monomeric or polymeric chain extender having at least one reactive hydroxyl groups and at least one reactive carboxyl group and that at least one terminal function of said macromolecule is a hydroxy group.

39. A process according to claim 1, wherein the phosphorous compound is selected from the group consisting of neopentylene-N,N-dimethylphosphoroamidite, o-phenylene-N,N-diisopropyl phosphoroamidite, di-(2-cyanoethyl)-N,N-diisopropylphosphoroamidite, dibenzyl-N,N-diethyl phosphoroamidite and hexamethylphosphorotriamide.

40. A process according to claim 28, wherein the phosphite is a trisphosphite of a monosaccharide, a sugar alcohol or an inositol yielding corresponding trisphosphate.

41. A process according to claim 11, wherein the hydroxy-functional compound is selected from the group consisting of 5-ethyl-5-methanol-1,3-dioxane, 2-ethyl-2-butyl-1,3-propanediol, neopentyl glycol, glycerol, trimethylolpropane, trimethylolethane, pentaerythritol, diglycerol, ditrimethylolpropane, ditrimethylolethane, dipentaethritol and tripentaerythritol.

42. A process according to claim 28, wherein the at least one oxidizing agent comprises at least one selected from the group consisting of peroxide, hydroperoxide, peracid, and the sulphur transferring reagent is elemental sulphur.

43. A process according to claim 1, wherein said process is performed at a temperature of −10° C. to 80° C.

44. A process according to claim 1, wherein said process is performed at a temperature of 0° C. to 40° C.

45. A process according claim 1, wherein the catalyst is present in an amount corresponding to 0.05 to 1 equivalents calculated on phosphorous equivalents.

46. A process according to claim 1, wherein the catalyst is present in an amount corresponding to 0.1 to 0.5 equivalents calculated on phosphorous equivalents.

47. A process according to claim 18, wherein the hydroxy-functional acid is selected from the group consisting of 2,2-dimethylolpropanoic acid, 3,5-dihydroxybenzoic acid, heptanoic acid and citric acid.

* * * * *